US008765632B2

(12) United States Patent
Zhang et al.

(10) Patent No.: US 8,765,632 B2
(45) Date of Patent: Jul. 1, 2014

(54) PROCESS FOR PREPARING CATALYST COMPRISING PALLADIUM SUPPORTED ON CARRIER WITH HIGH DISPERSION

(75) Inventors: Fazhi Zhang, Beijing (CN); Peng Chen, Beijing (CN); Rong Hou, Beijing (CN); Jiali Chen, Beijing (CN); Chao Gao, Beijing (CN); Hui Zhang, Beijing (CN); Dianqing Li, Beijing (CN); Feng Li, Beijing (CN); Xue Duan, Beijing (CN)

(73) Assignee: Beijing University of Chemical Technology, Beijing (CN)

( * ) Notice: Subject to any disclaimer, the term of this patent is extended or adjusted under 35 U.S.C. 154(b) by 303 days.

(21) Appl. No.: 13/128,546

(22) PCT Filed: Jun. 25, 2009

(86) PCT No.: PCT/CN2009/072453
§ 371 (c)(1),
(2), (4) Date: Jun. 8, 2011

(87) PCT Pub. No.: WO2010/054552
PCT Pub. Date: May 20, 2010

(65) Prior Publication Data
US 2011/0237430 A1    Sep. 29, 2011

(30) Foreign Application Priority Data
Nov. 13, 2008    (CN) .......................... 2008 1 0226494

(51) Int. Cl.
| | | |
|---|---|---|
| *B01J 23/00* | (2006.01) | |
| *B01J 23/02* | (2006.01) | |
| *B01J 23/08* | (2006.01) | |
| *B01J 23/40* | (2006.01) | |
| *B01J 23/42* | (2006.01) | |
| *B01J 23/44* | (2006.01) | |
| *B01J 20/00* | (2006.01) | |
| *B01J 21/04* | (2006.01) | |
| *B01J 31/00* | (2006.01) | |
| *B01J 37/00* | (2006.01) | |
| *C08F 4/02* | (2006.01) | |
| *C08F 4/60* | (2006.01) | |

(52) U.S. Cl.
USPC ........... 502/333; 502/104; 502/111; 502/327; 502/339; 502/355; 502/415; 502/439

(58) Field of Classification Search
USPC ......... 502/333, 339, 355, 415, 439, 104, 111, 502/327
See application file for complete search history.

(56) References Cited

U.S. PATENT DOCUMENTS 2,818,393 A * 12/1957 Lefrancois et al. ........... 502/334
3,842,017 A * 10/1974 Armistead et al. ............ 502/339
(Continued)

FOREIGN PATENT DOCUMENTS

| CN | 1269260 | 10/2000 |
|---|---|---|
| CN | 1483512 | 3/2004 |
| CN | 1483513 | 3/2004 |
| EP | 1 870 158 | 12/2007 |

OTHER PUBLICATIONS

Takehira, et al., "Mechanism of reconstitution of hydrotalcite leading to eggshell-type Ni loading on Mg-Al mixed oxide", Journal of Catalysis, vol. 231, No. 1, Apr. 2005, pp. 92-104—Abstract only.
International Search Report issued in International Application No. PCT/CN2009/072453, mailed Oct. 1, 2009, 6 pages.

*Primary Examiner* — Cam N. Nguyen
(74) *Attorney, Agent, or Firm* — Hamre, Schumann, Mueller & Larson, P.C.

(57) ABSTRACT

A process for preparing a catalyst comprising palladium supported on a carrier via a layered precursor, comprising the following steps: (1) synthesis of hydrotalcite layered precursor which comprises promoting metal element and aluminium on the surface of the carrier of $Al_2O_3$ microspheres, the atoms of the promoting metal and aluminium being highly dispersed by each other and bonded firmly to the carrier due to the crystal lattice positioning effect of the hydrotalcite crystal; (2) introduction of palladium into the carrier through impregnation; (3) drying; and (4) calcination and reduction with $H_2$, the hydrotalcite layered precursor being converted into a composite oxide which consists of oxides of the promoting metal and aluminium, and the promoting metal element and aluminium being highly dispersed by each other and being able to separate and disperse the mainly active palladium element loaded later. The process has the advantages of improving the catalytic performance of the catalyst, enhancing the stability of the catalyst, and achieving the object of reducing the consumption of the precious metal-palladium.

2 Claims, 2 Drawing Sheets

(56) References Cited

U.S. PATENT DOCUMENTS

| | | | |
|---|---|---|---|
| 4,113,658 A * | 9/1978 | Geus | 502/242 |
| 6,071,433 A | 6/2000 | Bhattacharyya | |
| 6,958,138 B1 * | 10/2005 | Devic | 423/584 |
| 2008/0124264 A1 * | 5/2008 | Ikeda et al. | 423/213.5 |
| 2009/0286678 A1 * | 11/2009 | Hagemeyer | 502/304 |

* cited by examiner

PROCESS FOR PREPARING CATALYST COMPRISING PALLADIUM SUPPORTED ON CARRIER WITH HIGH DISPERSION

FIELD OF THE INVENTION

The present invention relates to the field of catalyst technology, and particularly provides a preparation method of catalyst comprising palladium supported on a carrier with high dispersion.

BACKGROUND OF THE INVENTION

Supported catalysts have been largely applied in the petrochemical industry field, particularly in the hydrocarbon conversion, olefin selective oxidation, selective hydrogenation and other important reaction processes, because of their excellent heat and mass transfer performance, and the feature that can achieve continuous reaction easily. Their application account for more than 70% of the total catalyst.

In the preparation process of the supported catalysts used in the important petrochemical reactions, the immersion, spray and coating methods are usually used to add the supporting metal into the catalyst. By the use of above methods, the supported metals are easy to be influenced by the solvation effect and the cluster effect of the metal during the preparation process, and it is also easy to form the aggregation of the metal microcrystal in the followed calcination process, which may result in poor distribution of the supported metal and instability of the catalyst structure, low dispersion degree of the active metal, high energy consumption and large wastage of the noble metal.

Hydrotalcite-type composition include pure hydrotalcite or hydrotalcite-like compound, the host structure of hydrotalcite usually comprises two type of metal hydroxides, therefore hydrotalcite is also known as layered double hydroxides (LDHs). The intercalation composition of LDHs can be named as intercalated-LDHs. Hydrotalcite, hydrotalcite-like and intercalated-LDHs are generally named as LDH intercalation materials. These materials feature hexagonal lamellar structure, and the LDH sheets are high rigidity; therefore it is difficult to prepare the lamellar structure with controllable morphology. LDHs are one type of inorganic materials with unique structural characteristics, such as the elemental compositions and the pore structure can be tuned in a wide range, and the types of the interlayer anions can also be designed. These features supply a basis for LDHs to become the potential catalysts and the catalyst precursors in industry.

The public patent (CN 1269260A) describes a preparation method of the supported hydrotalcite. The method involves a simple one-dropping or double-dropping process to assemble the divalent-metal-containing LDH precursor at the surface and in the inner pore of the $Al_2O_3$ carrier through a reaction of the alkaline-earth metals and soluble trivalent metal salts. The calcination product of the LDH precursor exhibit a good catalysis activity in the alcohol/ether reaction of the formation of the amyl acetate. A literature (Journal of catalysis 231(2005) 92-104) reported that Ni metal supported on the Mg—Al composite oxides can enhance its activity as a catalyst. As well, because of the isolation effect on the metal atoms induced by the ion interaction in the LDH layer, this method can also enhance the catalysis performance and the stability of the catalyst, and play a positive role in reducing the consumption of the noble metals.

SUMMARY OF THE INVENTION

The method in this patent involves the formation of the hydrotalcite precursors containing the catalyst (promotor metals and aluminum elements) on the surface of the $Al_2O_3$ microspheres (carrier). The lattice localization effect of hydrotalcite can highly disperse the metal atoms (promotor) and aluminum atoms, which anchor firmly with the carrier; in the following process of the drying and calcination, the obtained hydrotalcite precursors transfer into composite oxides containing the promotor metal and aluminum with high dispersion, which can isolate and dilute the main active component palladium element that will be supported afterwards. This method can therefore enhance the total catalysis performance and the stability of the catalyst. In additional, this method can also decrease the consumption of the palladium noble metal.

The Detailed Steps of the Invention are as Follows:

1. The Preparation of the $M^{2+}Al$-LDHs/$Al_2O_3$ Precursors.

Weighting certain content of the urea and dissolving it into deionized water, where the obtained concentration of the urea is in the range 0.2~2 mol/L; Adding the $Al_2O_3$ carrier (mesh size: 26~100) with regular geometry into the above solution, where the adding content of the $Al_2O_3$ is 1~6 g/100 mL. Stirring the above solution at 80~150° C. for 3~15 hours to obtain a mixed solution. Weighting certain content of the soluble $M^{2+}$ salt into deionized water to form $M^{2+}$ solution. Based on a certain ratio, adding the $M^{2+}$ solution into the mixed solution, where the concentration of the $M^{2+}$ solution is in the range of 0.1~1 mol/L; stirring the obtained solution under 80~160° C. for 3~15 hours, after the process of cooling, filtration, and washed by the deionized water, the product is dried at 80~120° C., and the $M^{2+}Al$-LDHs/$Al_2O_3$ precursors can be obtained.

wherein the $M^{2+}$ is divalent cation, preferentially, $M^{2+}$ can be one or more types of $Mg^{2+}$, $Ni^{2+}$, $Ca^{2+}$, $Pd^{2+}$ and $Cu^{2+}$; more preferentially, $M^{2+}$ is one or more types of $Mg^{2+}$, $Ni^{2+}$, $Ca^{2+}$.

The as-mentioned sentence "the concentration of the $M^{2+}$ solution is in the range of 0.1~1 mol/L" means that the $M^{2+}$ ion is in the range of 0.1~1 mol/L in the mixed solution when no chemical reaction occur in the whole system.

wherein the shape of the $Al_2O_3$ carrier can be one or more types of spherical shape, clover or sheet-like shapes; the crystalline form of the $Al_2O_3$ carrier can be one or more types of $\delta$, $\beta$, $\gamma$, $\theta$ and $\eta$.

X-ray diffraction (XRD), fourier transform infrared (FT-IR), X-ray photoelectron spectroscopy (XPS) and other characterization methods confirmed that the $M^{2+}Al$-LDHs mentioned in this innovation are located at the surface and in the inner pore of the $Al_2O_3$ carrier in the as-prepared $M^{2+}Al$-LDHs/$Al_2O_3$.

2. The Preparation of the Supported Catalyst.

Weighing certain quality of palladium chloride ($PdCl_2$) to form a $PdCl_2$ solution, wherein the obtained concentrations of $PdCl_2$ aqueous solution maintains at 0.03~0.3 mol/L; adding the $M^{2+}Al$-LDHs precursors in the step 1 into the $PdCl_2$ aqueous solution, and placing the solution into a shaker under 50~90° C. water bath for 1~24 hours; After the process of filtration, and washed by the deionized water, the product is dried at 80~120° C. Then, calcinating the product at 300~900° C. for 2~24 hours; then the product was treated by a reduction process in a fixed bed reduction equipment under $H_2$ atmosphere at 200~600° C. for 2~24 hours. The supported catalyst can be obtained.

By the use of the inductively coupled plasma emission spectroscopy, the content of Pd in the catalyst can be determined at 0.1-5 wt %.

Under the condition of the urea, the active layer of aluminum can be formed on the surface of aluminum oxide, so as to provide aluminum resources for the formation of the hydrotalcite precursor. The method in the present invention used a layered precursor method, which involves the formation of the precursor with layered structure on the surface of material firstly, then the layered structure gradually disappears in the following treatment. Therefore, this method can achieve the localization of the $M^{2+}$Al-LDHs at the surface and in the inner pore of the $Al_2O_3$ carrier, which is the character of this invention. Because of the lattice localization effect of LDHs, the supported metal and aluminum element distributed at the surface of the carrier can be restricted by the lattice and can be isolated orientationally and uniformly. In the following calcination process, the metal ion is not easy to move, and Pd element is dispersed and isolated effectively. Therefore, the supported metal and active metal can be steadily distributed at the surface of the carrier, which enhance the total stability and the catalysis performance of the catalyst, and further reduce the use of noble metal catalyst.

The as-prepared catalyst in this invent were further evaluated on the fixed bed micro-reactor catalytic hydrogenation equipment. The formation of the dimethyl 1, 4-cyclohexanedicarboxylate by the hydrogenation of the dimethyl terephthalate was chosen as the reaction system. The reactant conversion rate is 90~97%, and the selectivity is 90~98%; while using the Pd/$Al_2O_3$ catalyst prepared by the typical immersion method for the same reaction, the reaction conversion rate is 85~95%, and the selectivity is 75~88%. Therefore, it can be concluded that the Pd/$Al_2O_3$ catalyst prepared by the layered precursor method exhibit higher catalyst performance (hydrogenation reactant activity and selectivity) than that of the typical immersion method.

DETAILED DESCRIPTION OF THE EMBODIMENTS

Figure 1:
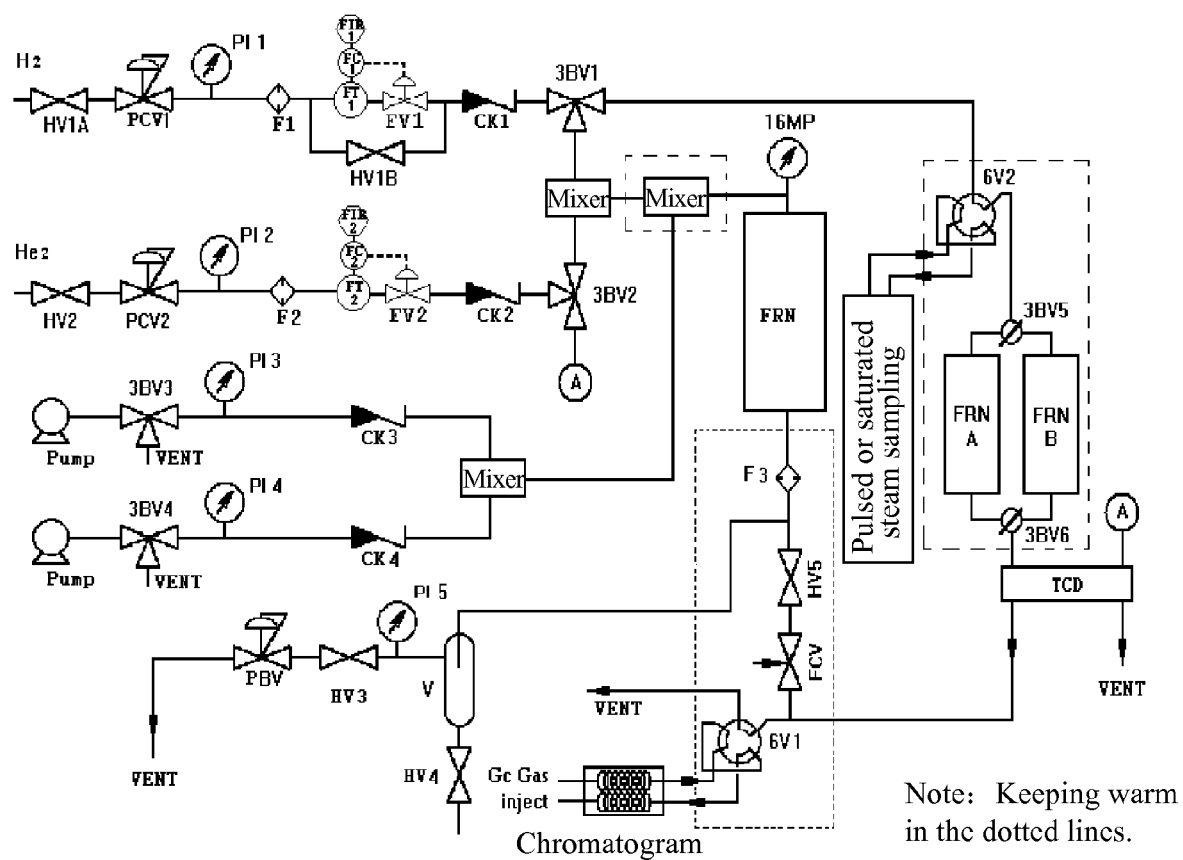
FIG. 1 is the schematic figure for the fixed bed microreactor catalytic hydrogenation equipment obtained from example 1-3.
Figure 2:
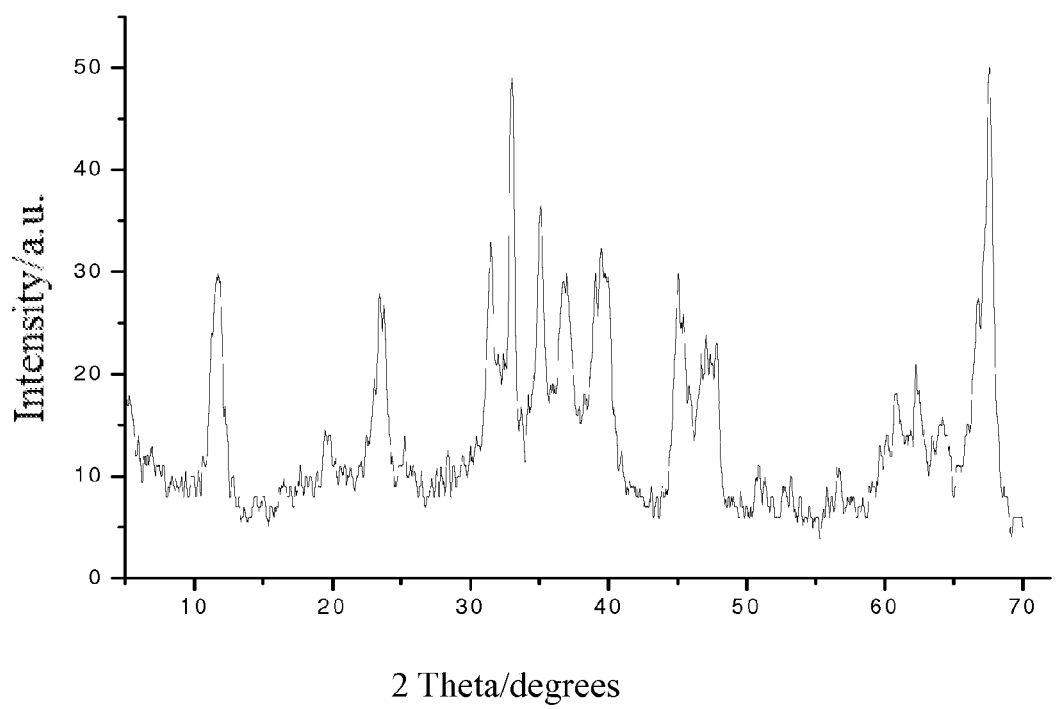
FIG. 2 is the XRD pattern of the as-prepared MgAl-LDHs/$Al_2O_3$ obtained from example 1.
Figure 3:
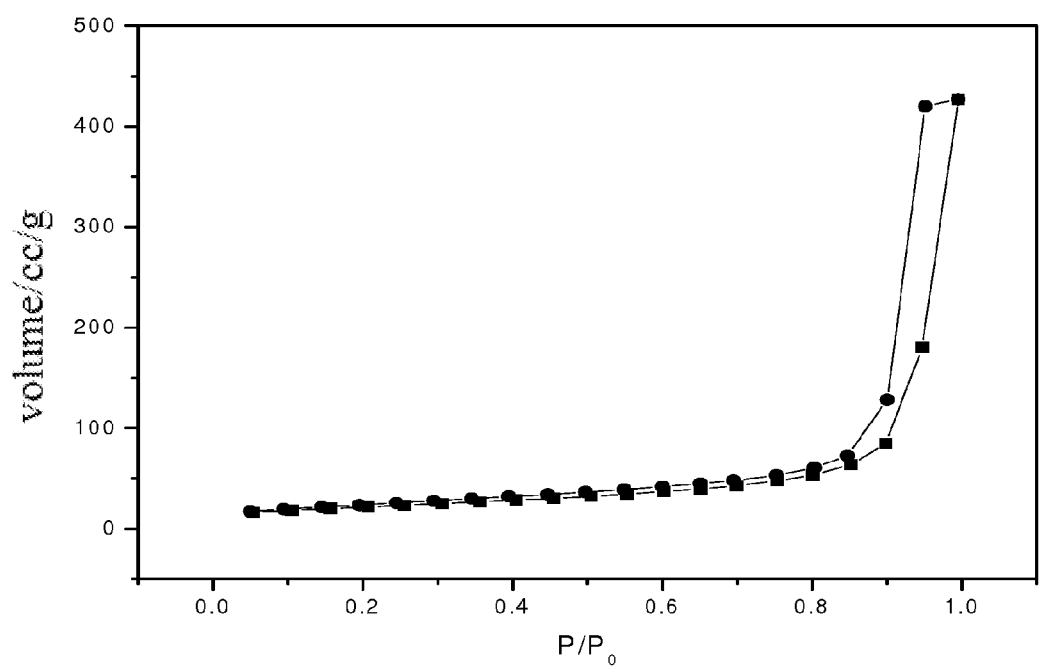
FIG. 3 is the nitrogen adsorption-desorption isotherm profile of the NiAl-LDHs/$Al_2O_3$ obtained from example 2; wherein P is nitrogen partial pressure, $P_0$ is the saturation vapor pressure for the tested materials.

The present invention will be further explained through following examples:

In the following examples, the products in this invent were measured by the following methods and instruments.

The structural analysis was performed on a Rigaku XRD-6000 X-ray diffractometer under air condition, using Cu Kα radiation (0.154 nm) at 40 kV, 30 mA with a continuous scanning rate of 2/min.

Pore structural analysis was performed on a S-IC-VP-type specific surface area-pore size distribution analyzer (Quanatachrome Instruments Company in US); the sample was degassed for 2 h at 373K in liquid nitrogen atmosphere for further nitrogen desorption test.

EXAMPLE 1

Weighting 4 g of the urea and dissolving it into deionized water to form 80 ml solution; Adding 2 g of the η-$Al_2O_3$ carrier (mesh size: 60) with spherical shape into the above solution, mixing the above solution at 130° C. for 12 hours. Weighting 12 g of the $Mg(NO_3)_2 \cdot 6H_2O$ into deionized water to form 20 mL solution and adding it into the mixture. Stirring the obtained solution under 130° C. for 12 hours, after the process of cooling, filtration, and washed by the deionized water, the product is dried at 80° C., and the MgAl-LDHs/$Al_2O_3$ precursor can be obtained.

Weighting 0.04 g of $PdCl_2$ to form a $PdCl_2$ solution,; adding the MgAl-LDHs/$Al_2O_3$ precursors into the $PdCl_2$ aqueous solution, and placing the solution into a shaker under 50° C. water bath for 24 hours; After the process of filtration, and washed by the deionized water, the solid product was dried at 80° C. Then, calcinating the product at 450° C. for 8 hours; the product was treated by a reduction process in a fixed bed reduction equipment under $H_2$ atmosphere at 300° C. for 3 hours. The supported catalyst can be obtained.

Based on the XRD profile, the obtained product is MgAl-LDHs/$Al_2O_3$.

Catalyst performance measurement: by the use of the fixed bed micro-reactor catalytic hydrogenation equipment (MRCS-2000DR micro-reactor chromatographic system), the obtained supported catalyst was used to catalyze the hydrogenation reaction of the dimethyl phthalate to form the 1,4-cyclohexanedicarboxylate. The reaction condition include: reaction temperature: 220° C.; pressure of the $H_2$: 80 atm; ratio of the hydrogen/oil: 80; solvent:ethyl acetate (100 ml/3 g dimethyl terephthalate); reaction time: 6 h. the reaction conversion rate of the dimethyl terephthalate is 91%, and the selectivity of the dimethyl 1,4-cyclohexanedicarboxylate is 98%.

COMPARATION EXAMPLE 1:

As a comparation, a catalyst was prepared by the immersion method through supporting 12 g of $Mg(NO_3)_2 \cdot 6H_2O$ and 0.04 g of $PdCl_2$ on the $Al_2O_3$ carrier. The catalysis performance was evaluated by the same method in the example 1. The reaction conversion rate of the dimethyl terephthalate is 88%, and the selectivity of the dimethyl 1,4-cyclohexanedicarboxylate is 80%.

EXAMPLE 2:

Weighting 8 g of the urea and dissolving it into deionized water to form 70 ml solution; Adding 3g of the θ-$Al_2O_3$ carrier (mesh size: 100) with spherical shape into the above solution, mixing the above solution at 100° C. for 15 hours. Weighting 16g of $Ni(NO_3)_2 \cdot 6H_2O$ into deionized water to form 30 mL solution and adding it into the mixture. Stirring the obtained solution under 110° C. for 14 hours, after the process of cooling, filtration, and washed by the deionized water, the product is dried at 100° C., and the NiAl-LDHs/$Al_2O_3$ precursor can be obtained.

Weighting 0.3 g of $PdCl_2$ to form a $PdCl_2$ solution,; adding the NiAl-LDHs/$Al_2O_3$ precursors into the $PdCl_2$ aqueous solution, and placing the solution into a shaker under 80° C. water bath for 12 hours; After the process of filtration, and washed by the deionized water, the solid product was dried at 120° C. Then, calcinating the product at 500° C. for 6 hours; then the product was treated by a reduction process in a fixed bed reduction equipment under $H_2$ atmosphere at 400° C. for 2.5 hours. The supported catalyst can be obtained.

Based on the XRD profile, the obtained product is NiAl-LDHs/$Al_2O_3$.

The catalysis performance was evaluated by the same method in the example 1. The reaction conversion rate of the dimethyl terephthalate is 90%, and the selectivity of the dimethyl 1,4-cyclohexanedicarboxylate is 94%.

COMPARATION EXAMPLE 2:

As a comparation, a catalyst was prepared by the immersion method through supporting 16 g of $Ni(NO_3)_2 \cdot 6H_2O$ and 0.3 g of $PdCl_2$ on the $Al_2O_3$ carrier. The catalysis performance was evaluated by the same method in the example 1. The reaction conversion rate of the dimethyl terephthalate is 92%, and the selectivity of the dimethyl 1,4-cyclohexanedicarboxylate is 88%.

EXAMPLE 3:

Weighting 6 g of the urea and dissolving it into deionized water to form 60 ml solution; Adding 3 g of the $\gamma$-$Al_2O_3$ carrier (mesh size: 40) with spherical shape into the above solution, mixing the above solution at 100° C. for 15 hours at 100° C. Weighting 9 g of $CaCl_2$ into deionized water to form 60 mL solution and adding it into the mixture. Stirring the obtained solution under 120° C. for 10 hours, after the process of cooling, filtration, and washed by the deionized water, the product is dried at 90° C., and the CaAl-LDHs/$Al_2O_3$ precursor can be obtained.

Weighing 0.3 g of $PdCl_2$ to form a $PdCl_2$ solution,; adding the CaAl-LDHs/$Al_2O_3$ precursors into the $PdCl_2$ aqueous solution, and placing the solution into a shaker under 90° C. water bath for 14 hours; After the process of filtration, and washed by the deionized water, the solid product was dried at 100° C. Then, calcinating the product at 400° C. for 9 hours; then the product was treated by a reduction process in a fixed bed reduction equipment under $H_2$ atmosphere at 300° C. for 4 hours. The supported catalyst can be obtained.

Based on the XRD profile, the obtained product is CaAl-LDHs/$Al_2O_3$.

The catalysis performance was evaluated by the same method in the example 1. The reaction conversion rate of the dimethyl terephthalate is 92%, and the selectivity of the dimethyl 1,4-cyclohexanedicarboxylate is 90%.

COMPARATION EXAMPLE 3:

As a comparation, a catalyst was prepared by the immersion method through supporting 18 g of $CaCl_2$ and 0.3 g of $PdCl_2$ on the $Al_2O_3$ carrier. The catalysis performance was evaluated by the same method in the example 1. The reaction conversion rate of the dimethyl terephthalate is 85%, and the selectivity of the dimethyl 1,4-cyclohexanedicarboxylate is 78%.

The invention claimed is:

1. A process for preparing a supported catalyst containing palladium on a carrier, the process comprising:
   (1) preparing $M^{2+}$Al-LDHs/$Al_2O_3$ precursors, including:
      dissolving an amount of urea into deionized water to obtain a urea solution having a concentration of the urea in the range of 0.2 to 2 mol/L;
      adding $Al_2O_3$ carriers having a mesh size of 26 to 100 with a regular geometry into the urea solution to obtain a second solution, where the content of the $Al_2O_3$ carriers is 1 to 6 g/100 mL;
      stirring the second solution at 80 to 150° C. for 3 to 15 hours to obtain a mixed solution;
      preparing an $M^{2+}$ solution by adding an amount of a soluble $M^{2+}$ salt into deionized water;
      adding the $M^{2+}$ solution into the mixed solution, where the concentration of the $M^{2+}$ solution is in the range of 0.1 to 1 mol/L, stirring under 80 to 160° C. for 3 to 15 hours, cooling, filtering, washing with deionized water, and drying at 80 to 120° C. to thus obtain the $M^{2+}$Al-LDHs/$Al_2O_3$ precursors; and
   (2) preparing the supported catalyst, including:
      forming a palladium chloride ($PdCl_2$) aqueous solution, wherein the concentration of the $PdCl_2$ aqueous solution is at 0.03 to 0.3 mol/L;
      adding the $M^{2+}$Al-LDHs/$Al_2O_3$ precursors prepared in step (1) into the $PdCl_2$ aqueous solution to obtain a solution, and placing the obtained solution into a shaker under 50 to 90° C. water bath for 1 to 24 hours;
      filtering the obtained solution, washing with deionized water, drying at 80 to 120° C., and calcining at 300 to 900° C. for 2 to 24 hours to obtain a calcined product; and
      treating the calcined product by a reduction process under $H_2$ atmosphere at 200 to 600° C. for 2 to 24 hours to obtain the supported catalyst,
   wherein the shape of the $Al_2O_3$ carriers is one or more types of a spherical shape, a clover shape, and a sheet-like shape, and the crystalline form of the $Al_2O_3$ carriers is one or more types of $\delta, \beta, \gamma, \theta$ and $\eta$, and
   wherein $M^{2+}$ of the $M^{2+}$Al-LDHs/$Al_2O_3$ precursors is one or more types of $Mg^{2+}$, $Ni^{2+}$, $Ca^{2+}$ and $Cu^{2+}$.

2. The process according to claim 1, wherein treating by a reduction process includes reducing in a fixed bed microreactor.

* * * * *